United States Patent [19]

Muto et al.

[11] Patent Number: 4,639,522
[45] Date of Patent: Jan. 27, 1987

[54] 1-BENZYL-3,5-DIMETHYL-4-PIPERDYL ESTER OF A HANTZSCH DIHYDROPYRIDINE

[75] Inventors: Kenji Muto; Toru Sugaya, both of Shizuoka; Tokuyuki Kuroda, Susono; Tamotsu Hashimoto, Numazu; Koji Yamada; Nobuhiro Nakamizo, both of Machida; Minoru Watanabe, Tokyo, all of Japan

[73] Assignee: Kyowa Hakko Kogyo Co., Ltd., Tokyo, Japan

[21] Appl. No.: 829,179

[22] Filed: Feb. 14, 1986

Related U.S. Application Data

[63] Continuation-in-part of Ser. No. 542,185, Oct. 14, 1983, abandoned.

[30] Foreign Application Priority Data

Oct. 15, 1982 [JP] Japan ............................. 57-180615

[51] Int. Cl.[4] .................. C07D 401/12; A61K 31/455
[52] U.S. Cl. ...................................... 546/194; 546/187
[58] Field of Search ................. 546/194, 187; 514/318

[56] References Cited

U.S. PATENT DOCUMENTS 4,448,964 5/1984 Muto et al. .......................... 546/194

Primary Examiner—Henry R. Jiles
Assistant Examiner—Dale A. Bjorkman
Attorney, Agent, or Firm—Antonelli, Terry & Wands

[57] ABSTRACT

The compound of the formula

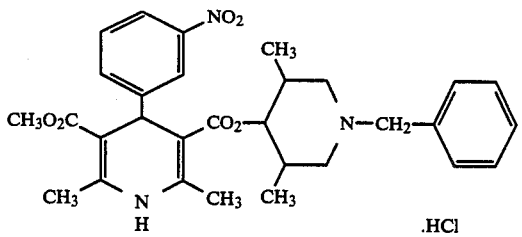

is disclosed to have a less rapid decrease in blood pressure in its use as an antihypertensive.

1 Claim, No Drawings

1-BENZYL-3,5-DIMETHYL-4-PIPERDYL ESTER OF A HANTZSCH DIHYDROPYRIDINE

This is a continuation-in-part of application Ser. No. 542,185, filed Oct. 14, 1983, abandoned.

The present invention relates to 1,4-dihydropyridine derivatives and pharmaceutically acceptable acid addition salts thereof. More specifically the present invention relates to a 1,4-dihydropyridine compound of the general formula (I) [hereinafter referred to as Compound (I)]:

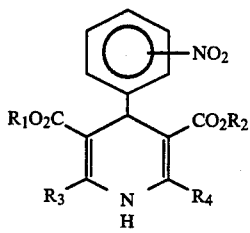

(I)

wherein one of $R_1$ and $R_2$ represents an alkyl group or a group of the general formula (II):

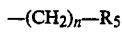

(II)

wherein $R_5$ represents an alkoxy group or a substituted or unsubstituted heterocyclic group and n represents 0 or an integer of 1-3, and the other of $R_1$ and $R_2$ represents a group of the general formula (III):

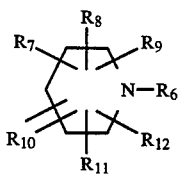

(III)

wherein $R_6$ represents a substituted or unsubstituted aralkyl group and $R_7$, $R_8$, $R_9$, $R_{10}$, $R_{11}$ and $R_{12}$ are the same or different groups and each represents hydrogen or an alkyl group, and two alkyl groups may be attached to one carbon atom on the piperidine ring, with the proviso that when $R_1$ is an alkyl group and $R_6$ is an unsubstituted aralkyl group, at least one of $R_7$, $R_8$, $R_9$, $R_{10}$, $R_{11}$ and $R_{12}$ represents an alkyl group, and $R_3$ and $R_4$ are the same or different groups and each represents an alkyl group, and pharmaceutically acceptable acid addition salts thereof.

There has always been a need for the development of compounds having excellent pharmaceutical activity. The present inventors, as the result of extensive studies for this purpose have found that the compounds represented by the general formula (I) have hypotensive activity, and thus have accomplished the present invention.

In the general formula (I), the alkyl groups for or represented by $R_1$, $R_2$, $R_3$, $R_4$, $R_7$, $R_8$, $R_9$, $R_{10}$, $R_{11}$ and $R_{12}$ include alkyl groups having 1-5 carbon atoms, such as a methyl group, an ethyl group, a propyl group, a butyl group and a pentyl group; the alkoxy group for $R_5$ includes alkoxy groups having 1-5 carbon atoms, such as a methoxy group, an ethoxy group, a propoxy group and a butoxy group; the heterocyclic group includes a thienyl group, a furyl group, a piperidyl group, a pyrrolidyl group, a pyranyl group, etc.; substituents for the substituted heterocyclic group include a hydrogen atom, alkyl groups having 1-5 carbon atoms such as a methyl group, an ethyl group, etc., aralkyl groups having 7-8 carbon atoms such as a benzyl group, a phenethyl group, etc. and the like; and examples of the substituted heterocyclic group include a tetrahydrofuryl group, a tetrahydrothienyl group, a tetrahydrothiopyranyl group, an N-methylpiperidyl group, an N-benzylpiperidyl group, etc.

The aralkyl group for $R_6$ includes aralkyl groups having 7-13 carbon atoms such as a benzyl group, a phenethyl group, a diphenylmethyl group, etc.; and substituents for the substituted aralkyl group for $R_6$ include halogen atoms such as fluorine, chlorine, bromine, iodine, etc., alkyl groups having 1-4 carbon atoms such as a methyl group, an ethyl group, a butyl group, etc., alkoxy groups having 1-4 carbon atoms such as a methoxy group, an ethoxy group, a butoxy group, etc., a phenyl group, a benzyl group, an amino group, a hydroxy group, a nitro group, etc.

The pharmaceutically acceptable acid addition salts of 1,4-dihydropyridine derivatives of the general formula (I) are inorganic acid salts such as hydrochlorides, hydrobromides, phosphates, sulfates, etc. and organic acid salts such as formates, acetates, fumarates, maleates, malates, aspartates, glutamates, etc.

Representative processes for production of the compounds of the present invention are illustrated below.

Process 1: [Process according to a process described by H. Herbert Fox, et al., J. Org. Chem. 16, 1259 (1951)]

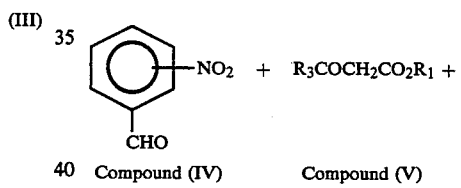

Compound (IV)    Compound (V)

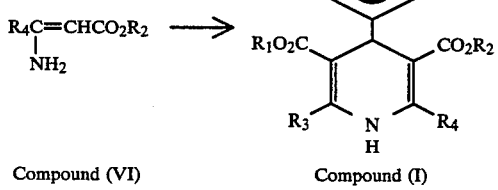

Compound (VI)    Compound (I)

wherein $R_1$, $R_2$, $R_3$ and $R_4$ have the same meaning as defined above.

The mixing molar ratio of the compounds (IV), (V) and (VI) is in the range of 1.0:0.8:0.8–1.0:4.0:4.0, preferably 1.0:0.9:0.9–1.0:1.5:1.5.

The reaction is carried out in the presence or absence of an alcohol such as methanol, ethanol, isopropanol, etc. an aromatic hydrocarbon such as benzene, toluene, etc. a halogenated hydrocarbon such as chloroform, carbon tetrachloride, etc. an ether such as tetrahydrofuran, dioxane, etc. an aprotic solvent such as acetonitrile, dimethylformamide, etc. or water at room temperature to 150° C., preferably 30°–100° C. Separation of the desired product from the reaction mixture is effected by the conventional operation such as concentration, extraction, column chromatography, crystallization, etc.

Process 2: [Process according to a process described by T. Shibanuma, et al., Chem. Pharm. Bull., 28, 2809 (1980)]

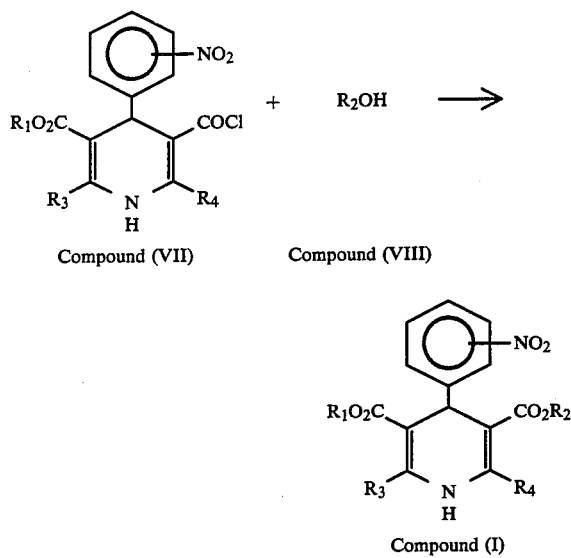

Compound (VII)    Compound (VIII)

Compound (I)

wherein $R_1$, $R_2$, $R_3$ and $R_4$ have the same meaning as defined above.

The mixing molar ratio of the compounds (VII) to (VIII) is in the range of 1.0:0.8–1.0:2.0, preferably 1.0:0.9–1.0:1.2.

The reaction is carried out in the presence or absence of a halogenated hydrocarbon such as dichloromethane, chloroform, carbon tetrachloride, chlorobenzene, etc. an aromatic hydrocarbon such as benzene, toluene, etc. an ether such as tetrahydrofuran, dioxane, etc. an aprotic polar solvent such as acetonitrile, dimethylformamide, etc. or an amine such as pyridine, triethylamine, etc. at $-70°$ C. to $100°$ C., preferably $-20°$ C. to $50°$ C. Separation of the desired product from the reaction mixture is effected by the conventional operation such as concentration, extraction, column chromatography, crystallization, etc.

The compounds (IV), (V), (VI), (VII) and (VIII) used as the starting materials in the present invention are either known compounds or obtained by the known processes [for example, A. B. Boese, Ind. Eng. Chem., 32, 16 (1940), S. A. Glickman, et al., J. Am. Chem. Soc., 67, 1017 (1945), J. H. Biel, et al., J. Org. Chem., 26, 4096 (1961), M. L. Drake, et al., J. Am. Chem. Soc., 77, 1204 (1955), etc.].

Typical examples of the compounds of the present invention are set forth in Table 1 and their structures in Table 2.

Compounds Nos. 1, 2, 3, ... 17 correspond to Example Nos. 1, 2, 3, ... 17 described hereinafter.

TABLE 1

| Compound No. | Name |
|---|---|
| 1 | 2,6-Dimethyl-4-(3-nitrophenyl)-1,4-dihydropyridine-3,5-dicarboxylic acid 3-(1-benzyl-3-methyl-4-piperidyl)-5-methyl ester |
| 2 | 2,6-Dimethyl-4-(3-nitrophenyl)-1,4-dihydropyridine-3,5-dicarboxylic acid 3-(1-benzyl-4-methyl-4-piperidyl)-5-methyl ester |
| 3 | 2,6-Dimethyl-4-(3-nitrophenyl)-1,4-dihydropyridine-3,5-dicarboxylic acid 3-(1-benzyl-3,5-dimethyl-4-piperidyl)-5-methyl ester |
| 4 | 2,6-Dimethyl-4-(3-nitrophenyl)-1,4-dihydropyridine-3,5-dicarboxylic acid 3-(1-benzyl-2,2,6,6-tetramethyl-4-piperidyl)-5-methyl ester |
| 5 | 2,6-Dimethyl-4-(3-nitrophenyl)-1,4-dihydropyridine-3,5-dicarboxylic acid 3-methyl-5-[3-methyl-1-(1-phenylethyl)-4-piperidyl] ester |
| 6 | 2,6-Dimethyl-4-(3-nitrophenyl)-1,4-dihydropyridine-3,5-dicarboxylic acid 3-methyl-5-[3,3-dimethyl-1-(1-phenylethyl)-4-piperidyl] ester |
| 7 | 2,6-Dimethyl-4-(3-nitrophenyl)-1,4-dihydropyridine-3,5-dicarboxylic acid 3-(1-benzyl-4-piperidyl)-5-tetrahydofurfuryl ester |
| 8 | 2,6-Dimethyl-4-(3-nitrophenyl)-1,4-dihydropyridine-3,5-dicarboxylic acid 3-(1-benzyl-4-piperidyl)-5-(2-ethoxyethyl) ester |
| 9 | 2,6-Dimethyl-4-(3-nitrophenyl)-1,4-dihydropyridine-3,5-dicarboxylic acid 3-(1-benzyl-4-piperidyl)-5-tetrahydrofuryl ester |
| 10 | 2,6-Dimethyl-4-(3-nitrophenyl)-1,4-dihydropyridine-3,5-dicarboxylic acid 3-(1-benzyl-4-piperidyl)-5-[2-(2-thienyl)ethyl] ester |
| 11 | 2,6-Dimethyl-4-(3-nitrophenyl)-1,4-dihydropyridine-3,5-dicarboxylic acid 3-methyl-5-[1-(3-methylbenzyl)-4-piperidyl] ester |
| 12 | 2,6-Dimethyl-4-(3-nitrophenyl)-1,4-dihydropyridine-3,5-dicarboxylic acid 3-[1-(3-chlorobenzyl)-4-piperidyl]-5-methyl ester |
| 13 | 2,6-Dimethyl-4-(3-nitrophenyl)-1,4-dihydropyridine-3,5-dicarboxylic acid 3-methyl-5-[1-(2,5-dimethylbenzyl)-4-piperidyl] ester |
| 14 | 2,6-Dimethyl-4-(3-nitrophenyl)-1,4-dihydropyridine-3,5-dicarboxylic acid 3-[1-(4-fluorobenzyl)-4-piperidyl]-5-methyl ester |
| 15 | 2,6-Dimethyl-4-(3-nitrophenyl)-1,4-dihydropyridine-3,5-dicarboxylic acid 3-methyl-5-[1-(4-methoxybenzyl)-4-piperidyl] ester |
| 16 | 2,6-Dimethyl-4-(3-nitrophenyl)-1,4-dihydropyridine-3,5-dicarboxylic acid 3-methyl-5-[1-(3,4,5-trimethoxybenzyl)-4-piperidyl] ester |
| 17 | 2,6-Dimethyl-4-(3-nitrophenyl)-1,4-dihydropyridine-3,5-dicarboxylic acid 3-[1-(4-fluorobenzyl)-3-piperidyl]-5-methyl ester |

TABLE 2

| Compound No. | $R_1$ | $R_2$ | $R_3$ | $R_4$ |
|---|---|---|---|---|
| 1 | $CH_3$ | A | $CH_3$ | $CH_3$ |
| 2 | " | B | " | " |
| 3 | " | D | " | " |
| 4 | " | E | " | " |
| 5 | " | F | " | " |
| 6 | " | G | " | " |
| 7 | P | K | " | " |
| 8 | Q | K | " | " |
| 9 | Y | K | " | " |
| 10 | Z | K | " | " |
| 11 | $CH_3$ | L | " | " |
| 12 | " | M | " | " |
| 13 | " | N | " | " |
| 14 | " | S | " | " |
| 15 | " | T | " | " |
| 16 | " | U | " | " |
| 17 | " | V | " | " |

Notes:

A: 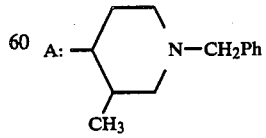

B: 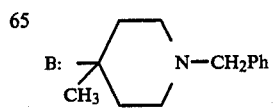

TABLE 2-continued

D: 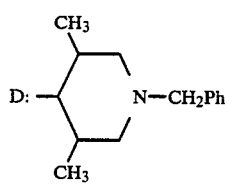

E: 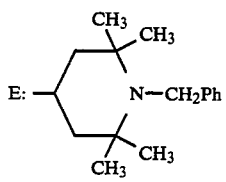

F: 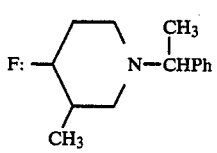

G: 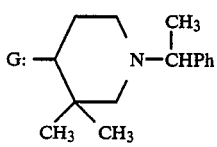

K: 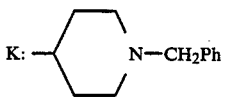

L: 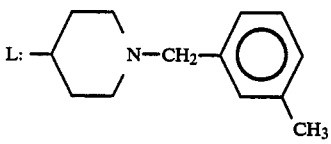

M: 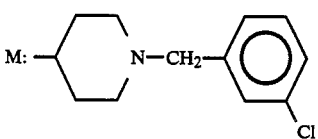

N: 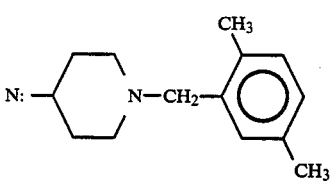

S: 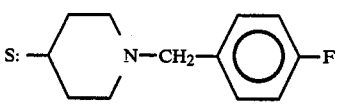

T: 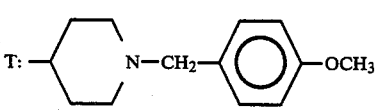

TABLE 2-continued

U: 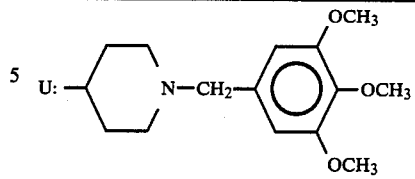

V: 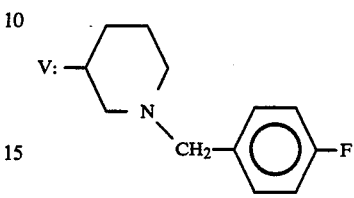

P: 

Q: CH$_3$CH$_2$OCH$_2$CH$_2$—

Y: 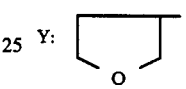

Z: 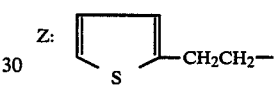

Ph: 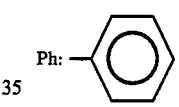

The hypotensive effect test of representative examples of the present compounds are given below.

Testing Method (for Compound Nos. 1, 2, 5–10)

Groups of 2 Wistar male rats weighing 150–200 g were used. The carotid artery of each rat was exposed under anesthetization with sodium pentobarbital (30 mg/kg, IP) and each cannula was planted chronically. On the following day, after confirming the recovery from the anesthetization, the blood pressure under non-anesthetic condition was hematoscopically measured on a Medical Corder, Nippon Kōden. Prior to the administration of the test compounds, rats exhibiting a blood pressure of 100–120 mmHg were chosen and used in the experiment.

The blood pressure was measured 3 times, i.e. 1, 3 and 5 hours after the administration of each test compound, and the judgement of the hypotension was such that test compounds indicating 10% or more reduction in blood pressure on at least two of three measurements when calculated by $$\frac{\text{Blood Pressure before Administration of the Test Compound} - \text{Blood Pressure after Administration}}{\text{Blood Pressure before Administration of the Test Compound}} \times 100$$

were considered to have the hypotension.

Further, from the presence or absence of the hypotension at each dose, the minimum effective dose (MED) was determined.

The results are shown in Table 3.

TABLE 3

| Compound No. | MED Showing 10% Reduction in Blood Pressure (mg/Kg) |
|---|---|
| 1 | 10 |
| 2 | 10 |
| 5 | 50 |
| 6 | 25 |
| 7 | 50 |
| 8 | 25 |
| 9 | 50 |
| 10 | 25 |

Testing Method (for Compound Nos. 11–15)

Groups, each of which was consisting of 2 spontaneously hypertensive rats (SHR) were used and the tail artery blood pressure was measured on a nonhemotoscopic blood pressure meter of Ueda Seisakusho.

Prior to the administration of the test compounds, rats showing a blood pressure of 180 mmHg or higher were chosen and used in the experiment.

The blood pressure was measured 1.5 hours after the administration of each test compound. The judgement of the blood pressure was such that test Compounds showing 15% or more reduction in blood pressure when calculated by $$\frac{\text{Blood Pressure before Administration of the Test Compound} - \text{Blood Pressure after Administration}}{\text{Blood Pressure before Administration of the Test Compound}} \times 100$$

were considered to have the hypotension.

Further, from the existence or non-existence of the hypotension at each dose, the minimum effective dose (MED) was determined.

The results are shown in Table 4.

TABLE 4

| Compound No. | MED Showing 15% Reduction in Blood Pressure (mg/Kg) |
|---|---|
| 11 | 10 |
| 12 | 2.5 |
| 13 | 10 |
| 14 | 1 |
| 15 | 10 |

The compounds of the present invention have not only a hypotensive effect but also effects to dilate coronary artery and peripheral blood vessels and thus are effective as drugs for cardiovascular disease.

The dose of these compounds to be administered to a human adult is 1–100 mg per day.

The compounds of the present invention, in consideration of their pharmaceutical effect, may be employed in various pharmaceutical forms for the intended administration, and in particular, they are preferably employed in oral forms such as tablets, powders, etc.

In the case of tablets, the compound of the present invention may be contained in an amount of 5–30% (W/W) per tablet. As other components (carriers), commonly employed excipients, disintegrators, lubricants, binders, coating agents, etc. may be employed.

For example, there may be mentioned excipients such as glucose, lactose, etc., disintegrators such as starch, calcium carboxymethyl cellulose, etc., lubricants such as magnesium stearate, talc, etc., binders such as simple syrup, polyvinyl alcohol, gelatin, hydroxypropyl cellulose, etc., and coating agents such as dispersants (e.g. methyl cellulose and ethyl cellulose) and plasticisers (e.g. glycerin and polyethylene glycol). Microcrystalline cellulose partakes of the properties of disintegrators of binders and of excipients.

In the case of powders, the compound of the present invention may be contained in an amount of 1–20% (W/W). As the carriers, excipients such as glucose, lactose, etc., binders such as hydroxypropyl cellulose, etc. and the like may be employed.

The present invention is more particularly described by the following examples and reference examples.

EXAMPLE 1

To 10 ml of tetrahydrofuran were added 1.65 g of m-nitrobenzaldehyde, 1.25 g of methyl β-aminocrotonate and 3.15 g of acetoacetic acid 1-benzyl-3-methyl-4-piperidyl ester obtained in Reference Example 1 described hereinafter. The mixture was stirred under reflux for 34 hours. After completion of the reaction, the reaction mixture was concentrated, and the concentrate was purified by silica gel column chromatography (eluent: chloroform:methanol=20:1 V/V) to obtain 3.15 g of a caramel-like product.

The caramel-like product was dissolved in 10 ml of acetone. The solution was acidified with 4 ml of ether saturated with hydrogen chloride, and concentrated again to obtain crude crystals. The crude crystals were recrystallized from ether to obtain 2.48 g of 2,6-dimethyl-4-(3-nitrophenyl)-1,4-dihydropyridine-3,5-dicarboxylic acid 3-(1-benzyl-3-methyl-4-piperidyl)-5-methyl ester hydrochloride.

Melting point: 141°–145° C.

NMR (DMSO-d$_6$) δ: 0.3–1.0(3H, m), 1.6–3.7(7H, broad), 2.30(6H, S), 3.60(3H, S), 4.20(2H, S), 4.2–5.0(1H, broad), 4.95(1H, S), 7.3–8.0(9H, m), 9.20(1H, broad).

EXAMPLE 2

At first, 4.89 g of 5-methoxycarbonyl-2,6-dimethyl-4-(3-nitrophenyl)-1,4-dihydropyridine-3-carboxylic acid [produced according to the process described in T. Shibanuma, et al., Chem. Pharm. Bull., 28, 2809 (1980)] was suspended in a mixed solvent of 20 ml of dichloromethane and 7.5 ml of dimethylformamide, and 1.96 g of thionyl chloride was added to the suspension under ice-cooling. After stirring for 2 hours, 3.39 g of 1-benzyl-4-hydroxy-4-methylpiperidine [produced according to the process described in J. M. McManus, et al., J. Med. Chem., 8, 765 (1965)] was added thereto, and stirred under ice-cooling for 2 hours and successively at room temperature for an hour. The reaction mixture was poured into 50 ml of an aqueous 5% sodium bicarbonate solution. The dichloromethane layer was dried over anhydrous sodium sulfate and concentrated. The concentrate was purified by silica gel column chromatography (eluent: chloroform:methanol=20:1 V/V) to obtain 3.89 g of a caramel-like product. The caramel-like product was dissolved in 10 ml of acetone, and 4 ml of ether saturated with hydrogen chloride and 50 ml of ethyl acetate were added to the solution to obtain crude crystals. The crude crystals were recrystallized from ethyl acetate to obtain 3.62 g of 2,6-dimethyl-4-(3-nitrophenyl)-1,4-dihydropyridine-3,5-dicarboxylic acid 3-(1-benzyl-4-methyl-4-piperidyl)-5-methyl ester hydrochloride.

Melting point: 207°–209° C.

NMR (HCl free, CDCl₃) δ: 1.40(3H, S), 1.5–2.8(8H, broad), 2.30(3H, S), 2.33(3H, S), 3.34(2H, S), 3.68(3H, S), 5.15(1H, S), 7.24(5H, S), 7.0–8.2(5H, m).

EXAMPLES 3–6

Procedures similar to those in Example 2 were employed except that the starting materials set forth in Table 5 were employed, whereby the desired products listed in Table 6 were obtained.

TABLE 5

| Example | Name | Amount Used (g) |
|---|---|---|
| 3 | 5-Methoxycarbonyl-2,6-dimethyl-4-(3-nitrophenyl)-1,4-dihydropyridine-3-carboxylic acid | 4.65 |
|   | Thionyl chloride | 1.67 |
|   | 1-Benzyl-4-hydroxy-3,5-dimethylpiperidine (obtained in Reference Example 3) | 3.14 |
| 4 | 5-Methoxycarbonyl-2,6-dimethyl-4-(3-nitrophenyl)-1,4-dihydropyridine-3-carboxylic acid | 3.32 |
|   | Thionyl chloride | 1.30 |
|   | 1-Benzyl-4-hydroxy-2,2,6,6-tetramethyl-piperidine* | 2.73 |
| 5 | 5-Methoxycarbonyl-2,6-dimethyl-4-(3-nitrophenyl)-1,4-dihydropyridine-3-carboxylic acid | 4.55 |
|   | Thionyl chloride | 1.63 |
|   | 4-Hydroxy-3-methyl-1-(1-phenylethyl)piperidine (obtained in Reference Example 2) | 3.18 |
| 6 | 5-Methoxycarbonyl-2,6-dimethyl-4-(3-nitrophenyl)-1,4-dihydropyridine-3-carboxylic acid | 5.41 |
|   | Thionyl chloride | 1.94 |
|   | 4-Hydroxy-3,3-dimethyl-1-(1-phenylethyl)piperidine (obtained in Reference Example 2) | 3.80 |

*Produced according to the process described in M. L. Drake, et al., J. Am. Chem. Soc., 77, 1204 (1955)

TABLE 6

| Compound No. | Yield (g) | M.p. (°C.) | NMR (δ) |
|---|---|---|---|
| 3 (Hydrochloride) | 1.46 | 159–161 | DMSO-d₆ 0.2–1.0(6H, m), 1.7–2.6(2H, broad), 2.34(S) and 2.40(S) (6H), 2.7–3.7(4H, broad), 3.57(3H, S), 4.1–4.8 (3H, broad), 5.00(1H), 7.3–8.15(9H, m), 9.35(1H, S), 11.0–12.0(1H, broad) |
| 4 (Hydrochloride) | 3.33 | 175–177 | HCl free, CDCl₃ 1.07(12H, d.d.J = 9Hz, 2Hz), 1.4–2.1(4H, broad), 2.35(6H, S), 3.65(3H, S), 3.82(2H, S), 4.9–5.4(1H, broad), 5.12(1H, S), 6.35(1H, S), 7.1–8.1(9H, m) |
| 5 (Hydrochloride) | 1.33 | — (amorphous) | HCl free, CDCl₃ 0.3–1.0(3H, m), 1.35(3H, d), 1.5–3.1(7H, broad), 2.34(6H, S), 3.40(1H, q), 3.64(3H, S), 4.0–4.7(1H, broad), 5.10(1H, S), 6.13(1H, S), 7.25(5H, S), 7.1–8.2(4H, m) |
| 6 (Hydrochloride) | 8.71 | — (amorphous) | HCl free, CDCl₃ 0.6–1.1(6H, m), 1.28(3H, d), 1.5–2.9(12H, m), 3.1–3.5 (1H, broad), 3.63(S) and 3.67(S)(3H), 4.3–4.7(1H, broad), 5.12(1H, S), 7.1–8.2(10H, m) |

EXAMPLE 7

At first, 2.87 g of m-nitrobenzaldehyde, 3.53 g of tetrahydrofurfuryl acetoacetate and 5.21 g of β-aminocrotonic acid 1-benzyl-4-piperidyl ester were stirred in 15 ml of methanol under reflux for 8 hours. Thereafter, the reaction mixture was concentrated, and the desired product was separated by silica gel column chromatography (eluent: chloroform:methanol=20:1 V/V). The fraction containing the desired product was concentrated, then dissolved in acetone, and acidified with ether saturated with hydrogen chloride. The acidic solution was again concentrated, and thereafter crystallized from ethyl acetate-acetone to obtain 3.59 g of yellow crystals of 2,6-dimethyl-4-(3-nitrophenyl)-1,4-dihydropyridine-3,5-dicarboxylic acid 3-(1-benzyl-4-piperidyl)-5-tetrahydrofurfuryl ester hydrochloride.

Melting point: 197°–199° C.

NMR (HCl free, CDCl₃) δ: 1.4–2.9(12H, broad), 2.33(6H, S), 3.45(2H, S), 3.6–3.95(2H, t, broad), 4.06(3H, S, broad), 4.6–4.9(1H, broad), 5.17 (1H, S), 6.23(1H, S), 7.25(5H, S), 7.4–8.3(4H, m).

EXAMPLES 8–10

Procedures similar to those in Example 7 were conducted except that the starting materials set forth in Table 7 were employed, whereby the desired products set forth in Table 8 were obtained.

TABLE 7

| Example | Name | Amount Used (g) |
|---|---|---|
| 8 | m-Nitrobenzaldehyde | 3.02 |
|   | 2-Ethoxyethyl acetoacetate | 3.48 |
|   | β-Aminocrotonic acid 1-benzyl-4-piperidyl ester | 5.49 |
| 9 | m-Nitrobenzaldehyde | 4.53 |
|   | Tetrahydrofuryl acetoacetate | 4.87 |
|   | β-Aminocrotonic acid 1-benzyl-4-piperidyl ester | 8.23 |
| 10 | m-Nitrobenzaldehyde | 2.27 |
|   | 2-(2-Thienyl)ethyl acetoacetate | 3.18 |
|   | β-Aminocrotonic acid 1-benzyl-4-piperidyl ester | 4.12 |

TABLE 8

| Compound No. | Yield (g) | M.p. (°C.) | NMR (HCl free, CDCl₃, δ) |
|---|---|---|---|
| 8 (Hydrochloride) | 3.93 | 183–186 | 1.27(3H, t), 1.5–2.0(4H, broad), 2.0–2.9(4H, broad), 2.33(6H, S), 3.3–3.8(6H, m), 4.1–4.4(2H, m), 4.6–5.0(1H, broad), 5.13(1H, S), 6.75(1H, S), 7.23(5H, S), 7.4–8.3(4H, m) |
| 9 (Hydrochloride) | 3.70 | 167–171 | 1.4–2.9(10H, m), 2.32(6H, S), 3.44(2H, S), 3.5–4.1 (4H, m), 4.5–5.0(1H, broad), 5.05(1H, S), 5.1–5.5 (1H, broad), 6.51(1H, S), 7.24(5H, S), 7.4–8.3(4H, m) |

TABLE 8-continued

| Compound No. | Yield (g) | M.p. (°C.) | NMR (HCl free, CDCl₃, δ) |
|---|---|---|---|
| 10 (Hydrochloride) | 1.32 | 189–192 | 1.5–2.9(8H, broad), 2.32(6H, S), 3.13(2H, t), 3.44 (2H, S), 4.29(2H, t), 4.5–5.0(1H, broad), 5.13(1H, S), 6.40(1H, S), 6.7–8.3(7H, m), 7.27(5H, S) |

EXAMPLE 11

At first, 4.00 g of 5-methoxycarbonyl-2,6-dimethyl-4-(3-nitrophenyl)-1,4-dihydropyridine-3-carboxylic acid was suspended in a mixed solvent of 9 ml of N,N-dimethylformamide and 32 ml of dichloromethane. Thereafter, 1.44 g of thionyl chloride was added to the suspension under ice-cooling. After stirring for an hour, a solution of 2.48 g of 4-hydroxy-1-(3-methylbenzyl)-piperidine in 10 ml of dichloromethane was added thereto, and the mixture was stirred under ice-cooling for 3.5 hours. To the reaction mixture was added an aqueous 5% sodium carbonate solution, the mixture was extracted with chloroform and the chloroform layer was washed with brine. The chloroform layer was concentrated, then the desired product was separated by silica gel column chromatography (eluent: chloroform:methanol=9:1 V/V), and the fraction containing the desired product was concentrated. The concentrate was dissolved in chloroform, acidified with ether saturated with hydrogen chloride, and washed with water. Thereafter, the chloroform was distilled off and crystallized from chloroform-ethyl acetate to obtain 3.49 g of yellow crystals of 2,6-dimethyl-4-(3-nitrophenyl)-1,4-dihydropyridine-3,5-dicarboxylic acid 3-methyl-5-[1-(3-methylbenzyl)-4-piperidyl] ester hydrochloride.

Melting point: 225°–226° C.

NMR (DMSO-d₆) δ: 1.6–2.7(4H, broad), 2.33(9H, S), 3.0–3.7(4H, broad), 3.56(3H, S), 4.21(2H, S), 4.5–5.1(2H), 7.1–8.1(8H, m), 9.25(1H, broad).

EXAMPLES 12–17

TABLE 9

| | Starting Materials | |
|---|---|---|
| Example | Name | Amount Used (g) |
| 12 | 5-Methoxycarbonyl-2,6-dimethyl-4-(3-nitrophenyl)-1,4-dihydropyridine-3-carboxylic acid | 3.32 |
| | Thionyl chloride | 1.19 |
| | 1-(3-Chlorobenzyl)-4-hydroxypiperidine | 2.37 |
| 13 | 5-Methoxycarbonyl-2,6-dimethyl-4-(3-nitrophenyl)-1,4-dihydropyridine-3-carboxylic acid | 3.32 |
| | Thionyl chloride | 1.19 |
| | 4-Hydroxy-1-(2,5-dimethylbenzyl)-piperidine | 2.30 |
| 14 | 5-Methoxycarbonyl-2,6-dimethyl-4-(3-nitrophenyl)-1,4-dihydropyridine-3-carboxylic acid | 3.32 |
| | Thionyl chloride | 1.19 |
| | 1-(4-Fluorobenzyl)-4-hydroxypiperidine | 2.20 |
| 15 | 5-Methoxycarbonyl-2,6-dimethyl-4-(3-nitrophenyl)-1,4-dihydropyridine-3-carboxylic acid | 1.93 |
| | Thionyl chloride | 0.69 |
| | 4-Hydroxy-1-(4-methoxybenzyl)piperidine | 1.35 |
| 16 | 5-Methoxycarbonyl-2,6-dimethyl-4-(3-nitrophenyl)-1,4-dihydropyridine-3-carboxylic acid | 4.00 |
| | Thionyl chloride | 1.43 |
| | 4-Hydroxy-1-(3,4,5-trimethoxybenzyl) piperidine | 3.71 |
| 17 | 5-Methoxycarbonyl-2,6-dimethyl-4-(3-nitrophenyl)-1,4-dihydropyridine-3-carboxylic acid | 3.32 |
| | Thionyl chloride | 1.25 |
| | 1-(4-Fluorobenzyl)-3-hydroxypiperidine | 2.09 |

TABLE 10

| Compound No. | Yield (g) | M.p. (°C.) | NMR (DMSO-d₆) δ |
|---|---|---|---|
| 12 | 2.23 | 258–260 | 1.6–2.7(4H, broad), 2.33(6H, S), 2.7–3.7(4H, broad), 3.57(3H, S), 4.32(2H, S), 4.6–5.1(1H, broad), 4.98 (1H, S), 7.3–8.1(8H, m), 9.2(1H, broad) |
| 13 | 2.54 | 226–229 | 1.7–2.7(16H, broad), 3.0–3.8(4H, broad), 3.57(3H, S), 4.25(2H, S, broad), 4.6–5.2(2H, broad), 7.05–8.1(7H, m), 9.35(1H, broad), 10.3–11.3(1H, broad) |
| 14 | 3.05 | 262–262.5 | 1.7–2.6(4H, broad), 2.31(6H, S), 2.7–3.7(4H, broad), 3.56(3H, S), 4.28(2H, S), 4.5–5.1(1H, broad), 4.97 (1H, S), 7.0–8.1(8H, m), 9.27(1H, broad), 10.9–11.7 (1H, broad) |
| 15 | 1.88 | 195–196 | 1.6–2.6(4H, broad), 2.33(6H, S), 2.7–3.9(4H, broad), 3.56(3H, S), 3.77(3H, S), 4.20(2H, S), 4.5–5.1(1H, broad), 4.96(1H, S), 6.85–8.1(8H, m), 9.30(1H, broad) |
| 16 | 3.21 | 185–186 | 1.5–2.6(4H, broad), 2.34(6H, S), 2.8–4.0(4H, broad), 3.58(3H, S), 3.70(3H, S), 3.83(6H, S), 4.20(2H, broad), 4.6–5.1(2H, broad), 7.09(2H, S), 7.5–8.2(4H, m), 9.3(1H, broad), 11.0–11.6(1H, broad) |
| 17 | 1.11 | 208–209 | 1.2–1.9(4H, broad), 2.1–2.9(4H, broad), 2.33(6H, S), 3.47(2H), 3.64(3H, S), 4.6–5.0(1H, broad), 5.08(1H, S), 6.11(1H, S), 6.7–8.2(8H, m), (HCl free, CDCl₃) |

Procedures similar to those in Example 11 were conducted except that the starting materials set forth in Table 9 were employed, whereby the desired products set forth in Table 10 were obtained.

REFERENCE EXAMPLE 1

At first, 4.2 g of 60% sodium hydride was suspended in 200 ml of tetrahydrofuran, and then a solution of 18.9 g of 1-benzyl-4-piperidone and 17.9 g of methyl iodide dissolved in 20 ml of tetrahydrofuran was added dropwise to the suspension at room temperature over 5 minutes. Thereafter, the mixture was heated to 60° C. and stirred for 5 hours. Thereafter, the reaction mixture was filtered. The filtrate was concentrated, and then the concentrate was poured into 150 ml of water and extracted with 120 ml portions of ethyl acetate three times. The extract was washed with 150 ml of brine, and then dried over anhydrous sodium sulfate. The solvent was distilled off under reduced pressure to obtain 21.6 g of an oily matter. The oily matter was purified by silica gel column chromatography (eluent: n-hexane:ethyl acetate=2:1 V/V) to obtain 8.0 g of 1-benzyl-3-methyl-4-piperidone.

Subsequently, 3.13 g of the 1-benzyl-3-methyl-4-piperidone obtained above was dissolved in 6 ml of ether. The solution was added dropwise to a suspension of 0.44 g of lithium aluminum hydride in 25 ml of ether over 5 minutes while maintaining the temperature at 24°–27° C. Then, the mixture was stirred at 25° C. for 10 minutes, and, 5 ml of water was added thereto under ice-cooling. The mixture was extracted with 30 ml of ether four times. The ether layer was washed with water, dried over anhydrous sodium sulfate and concentrated to obtain 3.17 g of an oily matter of 1-benzyl-4-hydroxy-3-methylpiperidine.

Further, 3.17 g of the 1-benzyl-4-hydroxy-3-methyl-piperidine obtained above and 1.36 g of diketene were stirred in 14 ml of tetrahydrofuran at 40° C. for 9 hours. The reaction mixture was concentrated under reduced pressure, and then purified by silica gel column chromatography (eluent: chloroform:methanol=30:1 V/V) to obtain 3.15 g of acetoacetic acid 1-benzyl-3-methyl-4-piperidyl ester.

NMR (CCl$_4$, $\delta$): 0.87(3H, d), 1.4–3.0(8H, broad), 2.18(3H, S), 3.30(2H, S), 3.42(2H, S), 4.2–4.7(1H, broad), 7.18(5H, S).

REFERENCE EXAMPLE 2

By procedures similar to those for the production of the intermediate 1-benzyl-4-hydroxy-3-methylpiperidine obtained in Reference Example 1, 5.0 g of 3-methyl-1-(1-phenylethyl)-4-piperidone and 9.0 g of 3,3-dimethyl-1-(1-phenylethyl)-4-piperidone were obtained from 20.3 g of 1-(1-phenylethyl)-4-piperidone and 15.7 g of methyl iodide. These compounds were reduced with lithium aluminum hydride respectively to obtain 4.1 g of 4-hydroxy-3-methyl-1-(1-phenylethyl)piperidine and 4.0 g of 4-hydroxy-3,3-dimethyl-1-(1-phenylethyl)-piperidine.

NMR (CDCl$_3$, $\delta$): 4-Hydroxy-3-methyl-1-(1-phenylethyl)piperidine: 0.90(3H), 1.37(2H, d), 1.2–2.3(5H, broad), 2.4–3.2(4H, broad), 3.40(1H, q), 7.21(5H, S).
4-Hydroxy-3,3-dimethyl-1-(1-phenylethyl)piperidine: 0.8–1.1(6H), 1.26(3H, d), 1.5–2.9(7H, m), 3.0–3.5(2H, m), 7.23(5H, S).

REFERENCE EXAMPLE 3

At first, 5.1 g of the intermediate 1-benzyl-3-methyl-4-piperidone obtained in Reference Example 1 and 6.0 g of N,N-dimethylhydrazine were stirred in 10 ml of ethanol under reflux for 9 hours, and then concentrated under reduced pressure to obtain 6.1 g of 1-benzyl-3-methyl-4-piperidone-N,N-dimethylhydrazone.

Subsequently, 6.1 g of the 1-benzyl-3-methyl-4-piperidone-N,N-dimethylhydrazone obtained above was dissolved in 30 ml of tetrahydrofuran. The solution were added dropwise to a solution of lithium diisopropylamide in tetrahydrofuran obtained from 23 ml of methyl lithium (1.2M ether solution), 3.8 ml of diisopropylamine and 30 ml of tetrahydrofuran at $-8°$ C. over 15 minutes and the mixture was stirred at the same temperature for 2 hours. Thereafter, the reaction mixture was cooled to $-60°$ C. and, to the reaction mixture was added 2.4 ml of methyl iodide. The temperature was gradually raised to 0° C. in 4 hours. The reaction mixture was poured into a mixed solvent of 120 ml of dichloromethane and 40 ml of water, and the dichloromethane layer was dried over anhydrous sodium sulfate and concentrated under reduced pressure. The concentrate was purified by silica gel column chromatography (eluent: chloroform:methanol=20:1 V/V) to obtain 3.8 g of 1-benzyl-3,5-dimethyl-4-piperidone.

Further, 3.8 g of the 1-bnezyl-3,5-dimethyl-4-piperidone obtained above was reduced with lithium aluminum hydride similarly as in Reference Example 1 to obtain 3.5 g of 1-benzyl-4-hydroxy-3,5-dimethylpiperidine.

NMR (CCl$_4$, $\delta$): 0.7–1.2(6H), 1.4–2.9(7H, broad), 3.3–3.8(3H), 7.13(5H, S).

EXAMPLE 18

In this example an experiment is conducted to show yet another advantage of the compounds of the present invention; namely, the compounds have a superior effect in that the rate of decrease in blood pressure for the initial or earlier period of administration is slow as compared with other compounds having a hypotensive effect especially those disclosed in U.S. Pat. No. 4,448,964 to Muto et al. In this experiment a test compound of the invention and a reference compound disclosed in Example 1 of U.S. Pat. No. 4,448,964 are evaluated to determine the hypotensive effect of each over a period of six hours by the following procedure:

To spontaneous hypertensive rats (SHR) is administered orally a suspension of a test compound in a 0.5% CMC physiological saline, and the systolic pressure of the tail artery is measured on an auto hemodinatometric recorder (Ueda Seisaku-sho).

The results are given in Table 11 wherein the test compound and the reference compound are compared.

TABLE 11

| Compound | Dose mg/kg | No. of Animals | Pressure before Administration (mmHg) | Change in Pressure (Pressure before administration − Pressure after administration mmHg) | | | | | | | | | | |
|---|---|---|---|---|---|---|---|---|---|---|---|---|---|---|
| | | | | 10 min | 20 min | 30 min | 40 min | 50 min | 1 hr | 2 hr | 3 hr | 4 hr | 5 hr | 6 hr |
| Test Compound (1) | 7.5 | 3 | 185 ± 6 | 19 ± 2 | 32 ± 9 | 43 ± 11 | 46 ± 9 | 49 ± 6 | 47 ± 7 | 32 ± 8 | 26 ± 8 | 33 ± 7 | 27 ± 3 | 28 ± 4 |
| Reference Com- | 3 | 5 | 183 ± 8.8 | 44 ± 6.3 | — | 45 ± 6.3 | — | — | 28 ± 8.1 | 37 ± 9.4 | 31 ± 10.6 | 30 ± 9.1 | 23 ± 8.8 | — |

TABLE 11-continued

| Compound | Dose mg/kg | No. of Animals | Pressure before Administration (mmHg) | Change in Pressure (Pressure before administration − Pressure after administration mmHg) | | | | | | | | | | |
|---|---|---|---|---|---|---|---|---|---|---|---|---|---|---|
| | | | | 10 min | 20 min | 30 min | 40 min | 50 min | 1 hr | 2 hr | 3 hr | 4 hr | 5 hr | 6 hr |
| pound (2) | | | | | | | | | | | | | | |

(1) Test Compound; namely:
2,6-Dimethyl-4-(3-nitrophenyl)-1,4-dihydropyridine-3,5-dicarboxylic acid 3-(1-benzyl-3,5-dimethyl-4-piperidyl)-5-methyl ester hydrochloride
Formula:

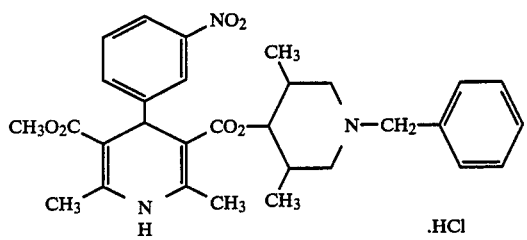

(2) Reference Compound; namely:
2,6-dimethyl-4-(3-nitrophenyl)-1,4-dihydropyridine-3,5-dicarboxylic acid-3-(N-benzyl-4-piperidinyl) ester-5-methyl ester hydrochloride
Formula:

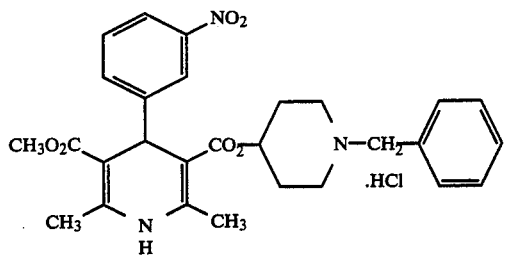

It is apparent from the result of this experiment and the data given in Table 11 above, that the rate of decrease in blood pressure for the earlier time (within 30 minutes) of the Test compound of the present invention is slow as compared with the reference compound as set forth in Example 1 of U.S. Pat. No. 4,448,964.

Consequently, side effects due to rapid decrease in blood pressure can be prevented.

Namely, the compound of the present invention is a superior drug for healing hypertension as compared with the reference compound.

What is claimed is:

1. A compound; namely, 2,6-dimethyl-4-(3-nitrophenyl)-1,4-dihydropyridine-3,5-dicarboxylic acid 3-(1-benzyl-3,5-dimethyl-4-piperidyl)-5-methyl ester hydrochloride.

* * * * *